United States Patent [19]

Hansen et al.

[11] 4,455,296

[45] Jun. 19, 1984

[54] HYBRID CELL LINES PRODUCING MONOCLONAL ANTIBODIES DIRECTED AGAINST *HAEMOPHILUS INFLUENZAE*

[75] Inventors: Eric J. Hansen, Plano; John R. Kettman, Carrollton; Stella M. Robertson, Plano, all of Tex.

[73] Assignee: Board of Regents, the University of Texas System, Austin, Tex.

[21] Appl. No.: 345,201

[22] Filed: Feb. 2, 1982

[51] Int. Cl.³ .................. A61K 39/40; A61K 39/395; C12N 5/00; C12N 15/00

[52] U.S. Cl. ........................................ 424/87; 424/85; 260/112 R; 260/112 B; 435/240; 435/172.2; 935/65; 935/99; 935/103; 935/108

[58] Field of Search ................................ 435/172, 240; 260/112 B, 112 R; 424/85, 87, 92

[56] References Cited

U.S. PATENT DOCUMENTS

| | | | |
|---|---|---|---|
| 4,172,124 | 10/1979 | Koprowski et al. | 424/85 |
| 4,196,265 | 4/1980 | Koprowski et al. | 435/2 |
| 4,271,145 | 6/1981 | Wands et al. | 424/85 |

OTHER PUBLICATIONS

Kennett, R., et al., Curr. Top, Microbiol, Immunol., vol. 81, pp. 77-91, 1978.
Glass, David, "Medicine's Micro Missiles", *Science Digest*, 30-31:114, (Jan. 1982).
Hansen, E. J., et al., "Detection of Anti-body Accessible Proteins on the Cell Surface of *Haemophilus influenzae* Type b," *Infection and Immunity*, vol. 33, No. 3, pp. 950-953, (Sep. 1981).
Hansen, E. J., et al., "Identification of Immunogenic Outer Membrane Proteins of *Haemophilus influenzae* Type b in the Infant Rat Model System," *Infection and Immunity*, vol. 32, No. 3, pp. 1084-1092.
Hansen, E. J., et al., "Isolation of Lymphocyte Hybridomas Producing Monoclonal Antibodies Specific for *Haemophilus influenzae* Type b Outer Membrane Antigens," *Amer. Soc. Micro*, B167; (Feb. 5, 1981).
Loeb, M. R., et al., "Outer Membrane Protein Composition in Disease Isolates of *Haemophilus influenzae*: Pathogenic and Epidemiological Implications," *Infection and Immunity*, vol. 30, No. 3, pp. 709-717 (Dec. 1980).

*Primary Examiner*—Blondel Hazel
*Attorney, Agent, or Firm*—Arnold, White & Durkee

[57] ABSTRACT

Continuous hybrid cell lines for producing monoclonal antibodies directed against outer membrane antigens of *Haemophilus influenzae* type b have been developed. The hybrid cell lines were established by fusing differentiated lymphoid cells primed with outer membrane antigens of *Haemophilus influenzae* type b with hybridoma cells. The resulting fused cells were cloned and characterized as to antibody specificity against antigenic determinants of outer membranes of *Haemophilus influenzae* type b. One hybrid produces a monoclonal antibody which is capable of conferring passive immunity on Hib infected hosts.

19 Claims, No Drawings

HYBRID CELL LINES PRODUCING MONOCLONAL ANTIBODIES DIRECTED AGAINST *HAEMOPHILUS INFLUENZAE*

The Government has rights in this invention pursuant to National Institutes of Health Grant Number AI-17621.

BACKGROUND OF THE INVENTION

The present invention relates to the production of monoclonal antibodies; and, in particular, to hybrid cell lines capable of continuously producing monoclonal antibodies directed against the outer membrane antigens of the bacterium *Haemophilus influenzae*.

In recent years, the capability to produce monoclonal antibodies specific for the immunogenic determinants of bacterial cells and toxins has provided a new vista of diagnostic and immunotherapeutic agents.

*Haemophilus influenzae* type b (Hib) is a bacterial pathogen attributed as the leading cause of endemic bacterial meningitis in infants and young children. This organism is also responsible for a number of other serious diseases in children, including epiglottitis and pneumonia.

The gravity of Hib meningitis is reflected by a mortality rate of 5-10%, despite treatment with antibiotics. Furthermore, a sizable percentage of survivors of Hib meningitis exhibit serious neurological sequelae. This situation, coupled with the recent emergence of ampicillin resistant strains of Hib, indicates the necessity for development of an effective vaccinogen to prevent Hib disease.

The currently available Hib vaccine featuring purified phosphoribosylribitol phosphate (PRRP) capsular antigen is not effective in inducing the formation of protective antibodies in children vaccinated at less than 14 months of age. Unfortunately, this group of children represents those persons at highest risk for systemic Hib disease.

Heretofore, it was generally assumed that serum antibody directed against the PRRP capsular element of Hib was responsible for resistance to Hib disease in humans. Recently, however, the protective value of anti-capsular antibody has been questioned, prompting the suggestion that antibody directed against somatic non-capsular Hib antigens may be equally or more important in providing resistance to Hib disease. In experiments designed to test prospective vaccinogens, infant rats which respond poorly to PRRP antigen mount a significant antibody response to general somatic non-capsular Hib antigens. However, the identity of the Hib cell surface immunogens to which these protective antibodies were directed had not been established prior to Applicant's work.

Two classes of Hib cell surface antigens against which protective antibodies might be directed include the lipopolysaccarides and proteins present in the outer membrane of the Hib pathogen. The inherent toxicity of most bacterial lipopolysaccharide molecules weighs against the implementation of this moiety as a potential Hib vaccinogen. In contrast, proteinaceous vaccines such as the diphtheria/pertussis/tetanus vaccine are relatively non-toxic and immunogenic in infants. Accordingly, the outer membrane proteins of Hib provide potential as a preferred agent for vaccinogens.

Conclusive proof that antibodies directed against Hib outer membrane antigens protect against systemic Hib disease requires the use of antibodies specific for these antigens. The recent development of lymphocyte hybridoma technology has made possible the production of monoclonal antibodies specific for any given antigen. While monoclonal antibodies have been extensively employed and manipulated in immunology, virology and parasitology research, research and application potential of monoclonal antibodies has only recently been tapped for microbial pathogenesis investigations. For example, monoclonal antibodies have been available for sometime now which are specific for an assortment of antigens, including viral antigens, such as rabies, hepatitis and influenza virus; red blood cells; fluorescent dyes; and cell associated antigens. More recently, monoclonal antibodies have been directed against bacterial components including different streptococcal antigens described by Briles et al, *J. Exp. Med.* 153:694–705 (1981) and Polin et al, *J. Clin. Microbiol.* 11:332–336 (1980); and cell surface antigens of *Neisseria gonorrhoeae* reported by Nachamkin et al, *Infect. Immun.* 32:641–648 (1981) and Johnston et al, *Abstr. Ann. Meet. Am. Soc. Microbiol.* B86, p. 29 (1981). Heretofore, as far as Applicants are aware, there have been no reports of the production of continuous cell lines of somatic cell hybrids which elaborate monoclonal antibodies to Hib outer membrane antigens, and in particular, to proteinaceous cell surface-exposed antigens.

It therefore is highly desirable to provide a means for producing antibody to outer membrane antigens of Hib. Such antibodies would be important in the diagnosis of Hib disease in humans, in the purification of specific immunogens for subsequent use as vaccines, and in use as highly specific immunotherapeutic agents to confer passive immunity on a host in the event of Hib infection.

SUMMARY OF THE INVENTION

In accordance with the present invention, continuous hybridoma cell lines are established which elaborate and secrete highly specific and homogenous monoclonal antibodies to various outer membrane antigens of *Haemophilis influenzae* bacteria.

In its broadest aspect, the invention involves first immunizing an animal to outer membrane antigens to develop lymphocytes and their differentiated progeny which produce antibodies directed against the desired antigen. The lymphocytes are recovered and fused with myeloma, plasmacytoma, or hybridoma cells to form somatic cell hybrids. The cell hybrids are cultured, selected, and propagated in tissue culture. Thereafter, the hybrid cell lines are capable of indefinitely producing monoclonal antibodies to the selected immunizing antigens. An outer membrane protein specific monoclonal antibody has been shown to be protective against experimentally induced *Haemophilus influenzae* disease. Furthermore, a monoclonal antibody derived from a selected hybridoma has been employed to purify an Hib outer membrane antigen bearing a single desired antigenic determinant, substantially free from other contaminating Haemophilus antigens.

DETAILED DESCRIPTION OF PREFERRED EMBODIMENTS

The following discussion is in terms of the preferred embodiments of this invention, which represent the best mode known to the Applicants at the time of this application.

In accordance with the processes of this invention, test animals are stimulated for antibody production by immunization with a preparation containing outer membrane components of *Haemophilus influenzae* type b. For example, the immunogen is suitably a substantially intact outer membrane vesicle, a heterogenous composition of disrupted outer membrane vesicles, the protein fraction of disrupted outer membrane vesicles, or a protein fraction of cell surface-exposed proteins from the outer membrane vesicles. Applicants have directed their preferred embodiment to immunization of mice with a heterogenous composition of disrupted outer membrane vesicles, thereby providing an exhaustive array of antigenic determinants.

Alternatively normal and immune differentiated lymphocytes capable of producing antibody can be isolated from test animals and cultured in vitro to generate cells appropriate for producing lymphocyte hybridomas, for example such methods as in vitro stimulation with mitogens and/or antigens as described by Robertson et al, *Microbiology* 1980 pp. 181–185 (1980) and Kettman et al, *J. Immunol. Methods* 39:203–222 (1980) or the method of splenic fragment culture as described by Press et al, *Eur. J. Immunol.* 4:155–159 (1974).

The route and schedule of immunization of the host animal or cultured antibody producing cells therefrom are generally in keeping with established and conventional techniques for antibody stimulation and production. Applicants have employed mice as the test model although it is contemplated that any mammalian subject including human subjects or antibody producing cells therefrom can be manipulated according to the processes of this invention to serve as the basis for production of human hybrid cell lines.

After immunization, immune lymphoid cells are fused with myeloma, plasmacytoma, or hybridoma cells (hereinafter referred to collectively as myeloma cells) to generate a hybrid cell line which can be cultivated and subcultivated indefinitely, to produce large quantities of monoclonal antibodies. For purposes of this invention, the immune lymphoid cells selected for fusion are lymphocytes and their normal differentiated progeny, taken either from lymph node tissue or spleens tissue from immunized animals. Applicants prefer to employ immune spleen cells, since they offer a more concentrated and convenient source of antibody producing cells with respect to the mouse system. The myeloma cells provide the basis for continuous propagation of the fused hybrid. Myeloma cells are tumor cells derived from plasma cells which show preference for bone marrow. Plasmacytoma cells are neoplastic cells derived from plasma cells. In particular, Applicants prefer to use lymphocyte hybridoma cells which secrete no immunoglobulin. Lymphocyte hybridoma cells are cells generated by the fusion of myeloma or plasmacytoma cells with normal differentiated lymphoid cells. Myeloma, plasmacytoma, and hybridomas can be selected to be devoid of immunoglobulin synthesis.

The particular species of animal from which the myeloma and immunized antibody producing cells are derived are not critical, in that it is possible to fuse cells of one species with another. However, it is preferred that the source of immunized antibody producing cells and myeloma be from the same species.

Generally the fusion techniques employed are according to the procedures set out by Kohler et al, *Eur. J. Immunol.* 6:11–19 (1976) and Kennett et al, *Lymphocyte Hybridomas—Current Topics in Microbiology and Immunology* 81:77–91 (1978) Springer-Verlag, New York. Fusion is generally accomplished by adding a suspension of antibody producing cells to the myeloma cells in growth medium and centrifuged to form a pellet.

The fused hybrids are next screened for antibody production specific for Hib outer membrane antigens. The outer membrane-specific monoclonal antibodies obtained according to preferred examples include antibodies with individual specificity for the numerous antigenic components of the outer membrane, including lipopolysaccharides, lipids, and protein antigenic determinants.

The hybridomas which secrete antibody specific for Hib outer membrane antigens are cultured to establish a continuous cell line with stable genetic coding. These cell lines can be stored and preserved in any of a number of conventional ways, including freezing and storage under liquid nitrogen. Frozen cell lines can be revived and cultured indefinitely with resumed synthesis and secretion of monoclonal antibodies specific for an outer membrane antigen. The secreted antibody is recovered from tissue culture supernatant by conventional precipitation, ion exchange, affinity chromatography, or the like. The recovered antibody can be freeze dried and stored under refrigeration for at least several weeks without significant loss of activity.

The following examples are offered to illustrate a particular embodiment of the invention but they are not intended to limit it.

A. Preparation of Antigens

The clinical bacterial strain isolate of Hib employed as a source of outer membrane vesicles was strain 26, which has been described previously, Hansen et al, *Infect. Immun.* 32:1084–1092 (1981). The other Hib strains used in these experiments were blood or cerebrospinal fluid isolates obtained from George H. McCracken, Jr., The University of Texas Health Science Center at Dallas. Hib was grown in liquid culture at 37° C. in Brain Heart Infusion (BHI) broth (Difco Laboratories, Detroit, Mich.) supplemented with Levinthal's Base (BHIs) furnishing a source of hemin and nicotinamide adenine dinucleotide. Stock cultures of all Hib strains were stored at $-70°$ C. in BHIs containing 30% (vol/vol) glycerol. For experimentation, all cultures were harvested in the logarithmic phase of growth.

The preparation of Hib outer membrane vesicles from intact Hib cells involved the lithium chloride extraction method of McDade et al, *J. Bacterol.* 141:1183–1191 (1980). Briefly, 10 gm (wet weight) of freshly harvested Hib cells were suspended in 200 ml of lithium chloride extraction buffer (200 mM LiCl, 100 mM lithium acetate (pH 6.0)) in a 500 ml flask containing approximately 100 glass beads (6 mm diameter). The suspended cells were agitated vigorously on a rotary shaker at 45° C. for 2 hr. The cell suspension was then carefully decanted, the glass beads washed three times with 25 ml LiCl extraction buffer, and these washings were added to the cell suspension which was then subjected to centrifugation at $12,000 \times g$ for 15 minutes. The resultant supernatant was carefully collected and subjected to centrifugation at $25,000 \times g$ for 15 minutes. The final supernatant fluid was passed over a Sepharose CL-6B column (Pharmacia, Piscataway, N.J.) and the void volume fraction, which contains the outer membrane vesicles, was collected and concentrated by vacuum dialysis against 50 mM Tris-HCl (pH 8.0). The protein content of the vesicle preparation was determined by the method of Markwell et al, *Anal. Biochem.* 87:206-210 (1978) and the vesicles were stored in multiple portions at −60° C. until used.

B. Immunization Schedule for Hybridoma Production

Several different immunization protocols were used to produce immune spleen cells for seven independent hybridization experiments. Six-to-eight week old BALB/cJ female mice (Jackson Laboratories, Bar Harbor, Maine) were injected intraperitoneally with Hib outer membrane vesicles (50 μg protein) suspended in 0.2 ml Freund's complete adjuvant (Difco Laboratories, Detroit, Mich.). Thirty days later, all immunized mice were given a second intraperitoneal injection with Hib outer membrane vesicles (30–40 μg protein) suspended in pH 7.2 phosphate-buffered saline (PBS). In addition, some mice were given a third intraperitoneal injection of Hib outer membrane vesicles (30-40 μg protein) 2-3 weeks after the second injection, and in one experiment, mice were given a fourth intravenous injection with Hib outer membrane vesicles (25 μg protein) 14 days after the third intraperitoneal injection. Spleens were removed for use in hybridoma production from the immunized mice three to four days after their last injection of antigen.

The Applicants have determined that immunizing mice by infecting them with viable, infectious Hib cells is a highly effective method for producing immune spleen cells for use in hybridoma construction. $10^7$ colony-forming units of Hib suspended in PBS containing 0.1% (wt/vol) gelatin were injected intraperitoneally into mice. Fourteen-fifteen days later, these mice were injected with $10^7$ Hib colony-forming units intraperitoneally or with $10^6$ Hib colony-forming units intravenously. Spleens were removed for use in hybridoma construction four days after the last injection of Hib cells.

C. Construction of Hybridomas

Hybridomas were produced by fusing spleen cells from the immunized mice with murine SP2/0-Ag14 hybridoma cells (SP2/0 hereinafter) using a modification of the basic procedure of Kennett et al, *Lymphocyte Hybridomas—Current Topics in Microbiology and Immunology*, Vol. 81, pp. 77–91 (1978) Springer-Verlag, New York. Suitable cell lines were obtained from Roger Kennett, University of Pennsylvania Medical School as originally set forth by Schulman et al, *Nature* 276:269–270 (1978). The SP2/0 hybridoma cell line is a hybrid cell line derived from SP2/HGLK formed as a hybrid between a BALB/c spleen cell and the myeloma cell line X63-Ag8. This cell line synthesizes no immunoglobulin chains, lacks the enzyme hypoxanthine guanine phosphoribosyl-transferase (HGPRT), is resistant to 8-azaguanine, and dies in the presence of Littlefield's hypoxanthine-aminopterinthymidine (HAT) selection medium. SP2/0 cells were grown in Dulbecco's Modified Eagle's Medium (DMEM) (Grand Island Biological Company, Grand Island, N.Y.) supplemented with 15% (vol/vol) heat-inactivated fetal calf serum (HyClone FCS; Sterile Systems, Logan, Utah), 2 mM L-glutamine, and 50 units/ml penicillin and 50 μg/ml streptomycin (GIBCO) (SDMEM). SP2/0 cells were grown in SDMEM containing 8-azaguanine (20 μg/ml) immediately prior to use in hybridization experiments to ensure that no HGPRT-positive revertants were present in the cell culture.

Spleens were removed aseptically from immunized mice and teased apart gently with forceps to prepare a single cell suspension in DMEM. SP2/0 cells were harvested in the logarithmic phase of growth and both cell types were collected by centrifugation at 270×g for 10 minutes at 8° C. and washed three times with DMEM. Total cell numbers were determined with a Coulter Counter Model ZF (Coulter Electronics, Inc., Atlanta, Ga.) and viability was measured by trypan blue exclusion.

Approximately $10^8$ spleen cells were mixed together with SP2/0 cells in a 50 ml conical tube at a ratio of 7-10 viable spleen cells per viable SP2/0 cell and the resultant cell suspension was collected in a pellet by centrifugation at 270×g for 10 minutes. The supernatant medium was removed and the tube containing the cell pellet was placed in a 37° C. water bath. A 0.2 ml portion of a warm (37° C.) 35% (wt/vol) solution of polyethylene glycol (PEG 1000; J. T. Baker Chemical Company, Phillipsburg, N.J.) in DMEM was added to the cell pellet which was then gently mixed with a glass rod. The cell suspension was incubated at 37° C. for 3 minutes and was then collected by centrifugation at 270×g for 4 minutes.

Warm DMEM (5 ml) was gently dropped onto the cell pellet which was then loosened with a glass rod. An additional 5 ml of warm DMEM was then added and the cells were collected by centrifugation. This final cell pellet was resuspended in 25-30 ml HY medium (see Kennett et al, supra at p. 78) and dispensed in 50 ul portions containing $1.6-5.3 \times 10^5$ cells each into microtiter plate wells (Costar Plastics, Vineland, N.J.), which were then incubated at 37° C. in a humidified incubator containing a 7% $CO_2$ atmosphere.

On day two, a 50 μl portion of a two-fold concentration of Littlefield's HAT selection medium specified in Littlefield et al, *Science* 145:709–710 (1964) was added to each well. An additional 100 μl portion of HAT was added to each well on day three.

The unfused SP2/0 cells died in HAT within 24–48 hours. Cell growth in HAT medium is indicative of successful hybridization. Hybrid clones selected in HAT were usually observed by day six. After day six, all wells were fed (HT)-glycine medium, which comprises HY medium containing $1.6 \times 10^{-5}$M thymidine, $1 \times 10^{-4}$M hypoxanthine, and $3 \times 10^{-6}$M glycine. Wells which contained growing clones were split 1:1 into two new microtiter wells and, if growth continued, cells were transferred from these two wells into one well of a 24-well tissue culture plate (Costar Plastics), from which supernatants were obtained for use in screening assays to detect monoclonal antibodies directed against Hib outer membrane antigens. Hybrid clones were maintained in SDMEM without feeder layers.

D. Characterization of Monoclonal Antibody

Analysis of Anti-Hib Outer Membrane Antigen Activity

Screening of hybrid clone culture supernatants for the presence of monoclonal antibodies directed against Hib outer membrane antigens was performed using an ELISA technique in essentially the same manner as described by Johnston, *Infect. Immun.* 28:101–110 (1980). Hib outer membrane vesicles (6 μg protein per well) employed as the source of antigen were coated onto microtiter wells in a 96-well plate (Costar Plastics) by the method of Voller et al, *Bull. WHO* 53:55–65 (1976). Antigen-coated wells were washed three times with pH 7.2 phosphate buffered saline (PBS) containing 0.05% (vol/vol) Tween 20 (PBS-Tween). PBS-Tween (300 μl) containing 1% (wt/vol) bovine serum albumin (BSA) was incubated in each microtiter well for 1 hour at room temperature to saturate nonspecific protein binding sites in the plastic well. This solution was then removed by aspiration, the wells were washed three times with PBS-Tween, 100 μl of hybrid clone culture supernatant was added to the well and the microtiter plate was incubated at 4° C. overnight. Positive control wells contained mouse serum obtained from the same mouse whose spleen was employed for hybridization.

Supernatant fluid was then removed by aspiration, the microtiter wells washed three times with PBS-Tween, and alkaline phosphatase-conjugated goat anti-mouse immunoglobulins (Cappel Laboratories, Cochranville, Pa.), prepared by the method of Voller et al, supra and diluted 1/400 in PBS-Tween, was then added to a final volume of 200 μl in each microtiter well. The microtiter plates were incubated at room temperature for one hour after which the conjugated antisera was removed by aspiration, the wells washed three times with PBS-Tween, and 300 μl of enzyme substrate [p-nitrophenyl phosphate (Sigma); 1 mg/ml in 10% (vol/vol) diethanolamine buffer (pH 9.8) containing 1 mM $MgCl_2$] was added to each well. Thirty minutes later, the absorbance of the solution in each well was determined spectrophotometrically at 405 nm using a Titetek Multiscan (Flow Laboratories, McLean, Va.). Microtiter wells in which the absorbance was at least two-fold greater than background levels of absorbance obtained with antigen-free control wells were scored as positive for the presence of antibodies directed against Hib outer membrane antigens.

Isotypic Analysis

Cultures positive for antibodies against Hib outer membranes were next tested to identify the mouse antibody isotype, using standard immunological assays employing rabbit and goat anti-mouse immunoglobulin (Ig) (Cappel Laboratories, Cochranville, Pa.). Affinity purified, heavy chain-specific rabbit anti-mouse subclass reagents were prepared for use as radioimmunoassay (RIA) probes. These reagents were prepared from antisera obtained from rabbits immunized with the following myeloma proteins: CBPC-22 (IgM); TEPC 15 (IgA); MOPC 21 (IgG1); UPC 10 (IgG2a); MOPC 195 (IgG2b); and FLOPC 21 (IgG3) (Cappel Laboratories). The immunoglobulin G (IgG) fraction was precipitated from the antisera at 4° C. with 37% (vol/vol) saturated ammonium sulfate and dialyzed against 0.01M sodium phosphate buffer (pH 7.5). The IgG fraction was further purified by batch elution from DEAE-Sepharose (Pharmacia) after 30 minute incubation at room temperature in 0.01M sodium phosphate buffer containing 0.05M NaCl. The Ig fraction was then absorbed over heterologous mouse Ig-Sepharose-CL4B (Pharmacia) columns to remove anti-light chain activity and any inappropriate anti-heavy chain activity. These antibodies were then affinity-purified on homologous mouse Ig-Sepharose-CL4B columns and eluted with either 0.2M propionic acid in 0.15M NaCl or 5M guanidine. After removal or neutralization of the eluting agent and concentration of the protein, these purified anti-subclass reagents were iodinated by a modification of the chloramine-T procedure, see Hunter et al, *Nature* 194:495–496 (1972).

Routine antibody subtyping was performed in a solid phase RIA. For subtyping, goat or rabbit anti-mouse Ig (1 mg/ml, 100 μl/well) was used to coat the microtiter plates. The plates were then washed and blocked with BSA as described above for the ELISA procedure. Culture supernatants were added and incubated for 3 hours at room temperature or 37° C. and then washed out. Iodinated affinity-purified rabbit anti-mouse isotype probes were added to identify the isotype of mouse antibody bound to the plate. The plates were incubated at 4° C., washed, cut and counted in a gamma counter. The isotypic characterizations of the hybrid clones evaluated are listed in Table 1.

Analysis of Anti-Hib Outer Membrane Protein Activity

Culture supernatant fluids from hybrid clones which scored positive in the ELISA test were assayed by a radioimmunoprecipitation method for the presence of monoclonal antibodies directed against Hib outer membrane proteins. Outer membrane proteins in intact cells of Hib were radioiodinated by the method of Hansen et al, *Infect. Immun.* 32:1084–1092 (1981).

Radioiodinated Hib cells (specific activity=0.01 counts/min/colony forming unit) were suspended to a final specific activity of $2 \times 10^7$ CPM per ml of solubilization buffer (SB) [10 mM Tris-HCl (pH 7.8) containing 150 mM NaCl, 10 mM ethylenediaminetetraacetic acid (EDTA), 1% (vol/vol) Triton X-100, 0.2% (wt/vol) sodium deoxycholate, and 0.1% (wt/vol) sodium dodecyl sulfate] and incubated at 37° C. for 60 minutes. Insoluble material was removed from suspension by centrifugation at 45,000×g for 1 hour at 20° C. The resultant supernatant containing solubilized radioiodinated Hib outer membrane proteins were divided into 500 μl portions containing $10^7$ CPM to which were added 500 μl portions of the hybrid clone supernatants. These mixtures were incubated for 2 hours at 4° C. with gentle agitation and then 10 μg of affinity-purified rabbit anti-mouse immunoglobulin was added to each tube as a probe for mouse monoclonal antibodies attached to Hib antigens.

After incubation of these mixtures for 1 hour at room temperature, 200 μl of a 10% (wt/vol) formalin-treated suspension of *Staphylococcus aureus* bearing Protein A on its surface (Staph A), prepared by the method of Kessler, *J. Immunol.* 117:1482–1490 (1976), was added to all reaction tubes which were then incubated at 4° C. with gentle agitation for 1 hour. The resultant (Staph A-antibody-antigen) complexes were washed five times with SB and processed for sodium dodecyl sulfate-polyacrylamide gel electrophoresis and autoradiographic analysis as described in Hansen et al, *Infect. Immun.* 32:1084–1092 and 33:950–953 (1981).

Seven different monoclonal antibodies (see Table 1) obtained from five different hybridization experiments were shown to be directed against Hib outer membrane proteins by means of the radioimmunoprecipitation system. Three different Hib outer membrane proteins with apparent molecular weights of 45,000, 39,000 and 37,000 were recognized by one or more of these monoclonal antibodies. These three proteins are quantitatively dominant in the LiCl-extracted outer membrane vesicles used to immunize mice for hybridoma production. Monoclonal antibody 2E10 (IgG2a) was specific for a Hib major outer membrane protein with an apparent molecular weight of 45,000. Monoclonal antibody 16C2 (IgG2b) was specific for a Hib major outer membrane protein with an apparent molecular weight of 37,000. The other five monoclonal antibodies, which could be divided into IgG and IgM isotypes (Table 1) and which were obtained from three independent hybridizations, were all directed against a Hib major outer membrane protein with an apparent molecular weight of 39,000 that has been shown in previous experiments by the Applicant, *Infect. Immun.* 33:950–953 (1981) to be at least partially exposed on the cell surface of Hib and accessible to antibody in this state. It is important to note further that all three of these Hib outer membrane proteins have been shown to be immunogenic in infant rats convalescing from systemic Hib disease, see Hansen et al, *Infect. Immuno.* 32:1084–1092 (1981).

TABLE 1

Monoclonal Antibodies Directed Against Hib Outer Membrane Proteins

| Hybrid Clone | Antibody Class | Outer Membrane Protein Antigen |
| --- | --- | --- |
| 17C4 | IgM | 39,000 M.W. |
| 6A2 | IgG3 | 39,000 M.W. |
| 5G6 | IgM | 39,000 M.W. |
| 2E10 | IgG2a | 45,000 M.W. |
| 8F8 | IgG3 | 39,000 M.W. |
| 17A10 | IgG2a | 39,000 M.W. |
| 16C2 | IgG2b | 37,000 M.W. |

Analysis of Anti-Hib Cell Surface-Exposed Protein Activity

The seven monoclonal antibodies listed in Table 1 that were shown to be directed against Hib outer membrane proteins were identified in radioimmunoprecipitation assays using solubilized Hib outer membrane proteins as antigen. In order to determine if any of these monoclonal antibodies were directed against cell surface-exposed portions of these outer membrane proteins, hybrid clone supernatants were adsorbed with intact Hib cells prior to use of these supernatants in radioimmunoprecipitation assays. Adsorption of hybrid clone culture supernatants with intact Hib cells was accomplished by incubating 200–500 μl of hybrid clone culture supernatant four times sequentially with $10^{10}$ intact, washed Hib cells for 1 hour at 4° C. Only one monoclonal antibody, 6A2, could be totally adsorbed out of the culture supernatants by intact Hib cells; the remaining six monoclonal antibodies were not completely adsorbed by Hib cells. Therefore, these latter six monoclonal antibodies are apparently directed at protein antigenic determinants which are either not exposed, partially exposed, or not accessible on the cell surface of intact Hib cells.

Confirmation that the protein antigenic determinant recognized by monoclonal antibody 6A2 is exposed on the surface of intact Hib cells was obtained by using 6A2 antibody in a radioimmunoprecipitation assay with intact, radioiodinated Hib cells. This radioimmunoprecipitation system, which involves incubation of whole Hib cells with antibody prior to solubilization of the Hib cells, has been previously shown to be specific for antibody-accessible proteins exposed on the Hib cell surface. Intact radioiodinated Hib cells ($2 \times 10^7$ cpm) were incubated with hybrid clone culture supernatants (500 μl) to detect monoclonal antibodies directed against cell surface-exposed antigenic determinants of Hib outer membrane proteins. Radioimmunoprecipitation analysis involving intact radioiodinated Hib cells as the antigen was performed exactly as described previously in *Infect. Immun.* 33:950–953 (1981) with the exception that affinity-purified rabbit anti-mouse immunoglobulin was used as a probe for mouse monoclonal antibodies, as described above.

When 6A2 antibody was employed in this latter radioimmunoprecipitation system, the same Hib major outer membrane protein (39,000 M.W.) immunoprecipitated by this antibody with pre-solubilized Hib cells was found in the resultant immune precipitate, indicating that 6A2 antibody does recognize and bind to a cell surface-exposed antigenic determinant of this protein. In contrast, 5G6 monoclonal antibody, which adsorption experiments indicated did not recognize a cell surface-exposed antigenic determinant of this same protein, did not precipitate this protein when used in this radioimmunoprecipitation system with intact, radioiodinated Hib cells.

A deposit of the hybrid cell line identified as 6A2 is on deposit with the American Type Culture Collection and is assigned the number ATCC CL HB8112.

Strain Distribution of the Antigenic Determinant Recognized by 6A2

It was of interest to determine if the antigenic determinant recognized by monoclonal antibody 6A2 was unique to the immunizing Hib strain or whether this antigenic determinant might be found in other Hib strains. Accordingly, six different clinical isolates of Hib (strains 26, TUR, HUG, TRA, PIP, and SAF) collected over a two year period were examined for the presence of the antigenic determinant recognized by monoclonal antibody 6A2. Small (200 μl) portions of 6A2 culture supernatant were adsorbed twice with $10^{10}$ intact cells of each Hib strain and the resultant preadsorbed 6A2 culture supernatants were employed in the standard ELISA assay used to detect monoclonal antibody activity directed against Hib outer membrane proteins. Intact cells of four of the six Hib strains adsorbed 6A2 monoclonal antibody to the same extent as Hib strain 26. Therefore, the cell surface-exposed protein antigenic determinant recognized by this monoclonal antibody is not unique to Hib strain 26 and is present in these four other Hib strains. These four Hib strains have been found to differ from both Hib strain 26 and each other by one or more proteins present in their outer membranes.

Development of a proteinaceous vaccine to protect against systemic Hib disease requires that the component protein(s) be common to, or antigenically cross-reactive with most if not all Hib strains. Previous studies have shown marked similarities and differences in the outer membrane protein content of clinical isolates of Hib but nothing was known about the degree of antigenic relatedness of these proteins. The fact that the antigenic determinant recognized by monoclonal antibody 6A2 is not unique to a single strain of Hib indicates that different Hib strains may share one or more protein antigens. This finding strengthens the possibility of identifying Hib cell surface-exposed outer membrane proteins which are common to, or antigenically cross-reactive in, most or all strains of Hib and which would be ideal candidates for Hib vaccinogens. This strategy to elucidate an effective vaccine for Hib disease underscores the research and bioanalytical usefulness and importance of the development of antibody producing hybrid cells against Hib outer membrane antigens.

E. Immunoprotection Against Hib Disease

Murine monoclonal antibody directed against a cell surface-exposed outer membrane protein of Hib was shown to provide protection against experimental disease induced by the Hib pathogen in an animal model system. Infant rats passively immunized with outer membrane protein-specific monoclonal antibody were protected against systemic Hib disease induced by intraperitoneal injection of virulent Hib cells.

In the example which follows, clinical isolates of Hib (strains 18, 26, and 72) provided by Dr. George McCracken, Jr., Department of Pediatrics, The University of Texas Health Science Center at Dallas, were employed to challenge infant rats passively immunized with monoclonal antibody 6A2. Monoclonal antibody 6A2 was purified from hybridoma culture supernatants by affinity chromatography using Protein A-Sepharose (Pharmacia Fine Chemicals, Piscataway, N.J.) by established methods. The standard protection experiment employed in this study was modified from the method of Granoff et al, *Infect. Immun.* 20:705–715 (1978). Eight-day old Sprague-Dawley infant rats (Charles River Breeding Farm, Wilmington, Mass.) were injected intraperitoneally with a 0.1 ml volume of either monoclonal antibody 6A2 (80 µl protein) or pH 7.2 (PBS). Six hours later, 100–200 Hib colony forming units were injected intraperitoneally into these animals. Bacteremia was quantitated 24 hours later by culturing 0.01 ml of blood obtained from the tail vein on BHIs agar plates. Hib colonies on these agar plates were identified by their characteristic iridescence in obliquely-reflected light. The lower limit of detection of Hib bacteremia in this model system is $10^2$ Hib colony forming units/ml blood.

Preliminary experiments established that systemic Hib disease, as evidenced by Hib bacteremia, could be produced in eight-day old infant rats by intraperitoneal injection of 100–200 colony forming units of Hib. The magnitude of bacteremia detected at 24 hour post-inoculation was always greater than $10^4$ colony forming units/ml blood.

Passive immunization of infant rats of intraperitoneal injection of antibody 6A2 (80 µg protein) six hours prior to infection with Hib strain 26 was shown to effectively protect these animals against systemic Hib disease. Antibody titration experiments established that as little as 5 ug of purified monoclonal antibody 6A2 successfully protects infant rats from developing detectable Hib bacteremia after challenge with Hib strain 26.

Infant rats passively immunized with monoclonal antibody 6A2 were relatively resistant to infection with Hib strain 18, which possesses the protein antigenic determinant recognized by monoclonal antibody 6A2; and the magnitude of bacteremia found in passively immunized animals that became infected was significantly lower than that seen in PBS-immunized control rats. In contrast, passive immunization of infant rat with monoclonal antibody 6A2 did not protect against infection with Hib strain 72, which lacks the antigenic determinant recognized by this monoclonal antibody.

In an alternate experiment, Hib bacteremia first was established in infant rats by intraperitoneal injection of 200 viable Hib strain 26 cells. The, at both 24 hours and 40 hours post-infection, 0.1 ml volumes of either monoclonal antibody 6A2 (80 µg protein) or PBS were injected intraperitoneally, and tail vein blood was sampled at 48 hours post-infection for detection of bacteremia.

This latter experiment showed that this monoclonal antibody was also effective in eliminating established Hib infection in the infant rat model system. Eight hours after infant rats with pre-existing Hib bacteremia received the last of two injections of monoclonal antibody 6A2, bacteremia was found to be present in only one-third of these animals, and the magnitude of bacteremia in these latter animals was two orders of magnitude lower than that observed in bacteremic control animals which received injections of PBS.

F. Utility

The hybridoma cell lines and the monoclonal antibodies produced therefrom described in this application are useful in the purification and characterization of specific antigenic and immunogenic components presented by the outer membrane of *Haemophilus influenzae* bacteria and in particular Hib. Moreover, the monoclonal antibodies produced from a given hybridoma line are homogeneous in antigenic recognition and thereby are useful for subsequent affinity chromatography-based purification of Hib outer membrane antigens.

Furthermore, the availability of different monoclonal abtibodies directed against one or more antigenic determinants of the same outer membrane antigen of Hib is useful in studying the structure and function of membrane components. Similarily, these same monoclonal antibodies are valuable in the idiotypic analysis of antibody response to cell surface structures of a pathogenic microorganism.

Ultimately, the availability of monoclonal antibodies directed against selected Hib outer membrane antigens, in particular cell surface-exposed membrane proteins, will facilitate studies on the vaccinogenic potential of these proteins.

The foregoing description of the invention has been directed to particular embodiments for purposes of explanation and illustration. It will be apparent, however, to those skilled in the art that many modifications and changes in the processes of preparing and implementing the described embodiments may be made without departing from the essence of the invention.

For example, it is contemplated that hybridoma cell lines may be developed fusing human myeloma cells and human lymphocytes primed to outer membrane antigens of Hib.

In another example, monoclonal antibodies can be developed which are specific for Hib strains other than strain 26. Also, hybridoma cells can be constructed from the differentiated lymphoid cells of mice immunized by alternate routes and methods; including systemic Hib infection. Similarly, other mouse strains can be used to produce hybridoma cells elaborating similar sets of monoclonal antibodies suitable to the purposes described herein. Moreover, monoclonal antibodies need not be limited against protein components of the outer membrane. Development of hybridoma producing antibody against lipopolysaccharide components of the outer membrane can be developed according to the processes of this invention. Such antibodies would be useful in the purification, isolation, and structural determination of the lipopolysaccharide layer exhibited by the outer membrane of the *Haemophilus influenzae* bacteria. These and other modifications and uses of the depicted embodiments, as well as other embodiments of the invention, will be apparent to those skilled in the art. It is Applicants' intention in the following claims to cover all equivalent modifications and variations as fall within the scope of the invention.

What is claimed is:

1. A composition of matter consisting essentially of a continuous hybrid cell line that produces monoclonal antibody to an outer membrane protein antigen of *Haemophilus influenzae* type b.

2. The composition of matter of claim 1 wherein the continuous hybrid cell line is together with a culture medium suitable for supporting growth of the cell line.

3. The composition of matter of claim 1 wherein the outer membrane antigen is a cell surface-exposed antigen.

4. The composition of matter of claim 1 wherein the outer membrane antigen is selected from the group consisting of outer membrane proteins having an apparent molecular weight of 45,000; 39,000; or 37,000.

5. The composition of matter of claim 1 wherein the outer membrane antigen is a cell surface-exposed protein having an apparent molecular weight of 39,000.

6. The composition of matter of claim 1 wherein the hybrid cell line is a cell hybrid of a differentiated lymphoid cell capable of producing antibodies against an outer membrane antigen of *Haemophilus influenzae* type b, fused to a myeloma cell.

7. The composition of matter of claim 6 wherein the myeloma cell is a plasmacytoma cell or hybridoma cell.

8. The composition of matter of claim 6 wherein the differentiated lymphoid cell is an immune spleen cell or lymph node cell.

9. The composition of matter of claim 1 wherein the continuous hybrid cell line is a cell hybrid of a BALB/cJ mouse immune spleen cell capable of producing antibody against *Haemophilus influenzae* type b, outer membrane, cell surface-exposed protein having an apparent molecular weight of 39,000, fused to a SP2/0 hybridoma cell.

10. The composition of matter of claim 1 wherein the hybrid cell line consists essentially of hybridoma clone 6A2.

11. The composition of matter of claim 1 wherein said antibody is an IgG molecule.

12. The composition of matter of claim 1 wherein said antibody is an IgM molecule.

13. A composition of matter consisting essentially of monoclonal antibodies directed against an outer membrane protein antigen of *Haemophilus influenzae* type b.

14. The composition of matter of claim 13 wherein the antibodies are directed against a cell surface-exposed antigen of *Haemophilus influenzae* type b.

15. The composition of matter of claim 13 wherein the antibodies are directed against a *Haemophilus influenzae* type b, outer membrane antigen selected from the group consisting of proteins having an apparent molecular weight of 45,000; 39,000; or 37,000.

16. The composition of matter of claim 13 wherein the antibodies are directed against a *Haemophilus influenzae* type b, outer membrane, cell surface-exposed protein having an apparent molecular weight of 39,000.

17. The composition of matter of claim 13 wherein the antibodies are IgG molecules.

18. The composition of matter of claim 13 wherein the antibodies are IgM molecules.

19. The composition of matter of claim 13 together with a physiologically compatible diluent, the composition adapted for use in passive immunization of a host suspected of having *Haemophilus influenzae* type b disease.

* * * * *